United States Patent
Shen et al.

(10) Patent No.: US 10,249,039 B2
(45) Date of Patent: Apr. 2, 2019

(54) SKIN CONDITION DETECTION METHOD, ELETRONIC APPARATUS, AND SKIN CONDITION DETECTION SYSTEM

(71) Applicant: CAL-COMP BIG DATA, INC., New Taipei (TW)

(72) Inventors: Shyh-Yong Shen, New Taipei (TW); Min-Chang Chi, New Taipei (TW); Yung-Hsuan Lin, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 8 days.

(21) Appl. No.: 15/648,454

(22) Filed: Jul. 12, 2017

(65) Prior Publication Data
US 2018/0357761 A1    Dec. 13, 2018

(30) Foreign Application Priority Data
Jun. 9, 2017    (CN) .......................... 2017 1 0430938

(51) Int. Cl.
| | | |
|---|---|---|
| *G06K 9/00* | (2006.01) | |
| *G06T 7/00* | (2017.01) | |
| *A61B 5/00* | (2006.01) | |

(52) U.S. Cl.
CPC ............ *G06T 7/0012* (2013.01); *A61B 5/441* (2013.01); *A61B 5/74* (2013.01); *A61B 5/0077* (2013.01); *A61B 5/443* (2013.01); *A61B 5/68* (2013.01); *A61B 5/684* (2013.01); *A61B 5/6814* (2013.01); *A61B 5/7475* (2013.01); *G06T 2207/30088* (2013.01); *G06T 2207/30201* (2013.01)

(58) Field of Classification Search
CPC ..... A61B 5/14532; A61B 5/01; A61B 5/0022; A61B 5/411; A61B 5/4866
USPC .......... 382/128; 600/300, 306, 547; 345/619
See application file for complete search history.

(56) References Cited

U.S. PATENT DOCUMENTS

| | | | | |
|---|---|---|---|---|
| 5,938,593 | A * | 8/1999 | Ouellette | A61B 5/0531 324/692 |
| 2008/0194928 | A1* | 8/2008 | Bandic | G16H 15/00 600/306 |

(Continued)

FOREIGN PATENT DOCUMENTS

WO    2016199134    12/2016

OTHER PUBLICATIONS

"Search Report of Europe Counterpart Application", dated Mar. 29, 2018, p. 1-p. 9.

*Primary Examiner* — Charlotte M Baker
(74) *Attorney, Agent, or Firm* — JCIPRNET

(57) ABSTRACT

A skin condition detection method adapted to detect a skin condition of each of a plurality of facial areas by a detection apparatus is provided. The skin condition detection method includes the following steps: providing an action prompt that prompts to place the detection apparatus on one of the facial areas; detecting a user action corresponding to the detection apparatus; determining if the user action including the detection apparatus corresponds to the facial area prompted by the action prompt; and when the user action including the detection apparatus corresponds to the facial area prompted by the action prompt, analyzing the skin condition of the facial area by a skin analysis method corresponding to the facial area. In addition, an electronic apparatus and a skin condition detection system using the skin condition detection method are also provided.

9 Claims, 4 Drawing Sheets

(56) References Cited

U.S. PATENT DOCUMENTS

| | | |
|---|---|---|
| 2011/0116691 A1 | 5/2011 | Chung et al. |
| 2014/0304629 A1 | 10/2014 | Cummins et al. |
| 2015/0213619 A1 | 7/2015 | Nakamura et al. |
| 2017/0119301 A1 | 5/2017 | Kimura |

* cited by examiner

SKIN CONDITION DETECTION METHOD, ELETRONIC APPARATUS, AND SKIN CONDITION DETECTION SYSTEM

CROSS-REFERENCE TO RELATED APPLICATION

This application claims the priority benefit of Chinese application serial no. 201710430938.0, filed on Jun. 9, 2017. The entirety of the above-mentioned patent application is hereby incorporated by reference herein and made a part of this specification.

BACKGROUND OF THE INVENTION

Field of the Invention

The invention relates to a skin condition detection method, an electronic apparatus, and a skin condition detection system.

Description of Related Art

The normal stratum corneum of skin has a moisture content of about 20% to 35%. When the moisture content is below 10%, the stratum corneum is in a dry state. Not only does the skin become dry and tight, skin brightness also relatively declines so that the skin looks dull. Besides, when the stratum corneum lacks moisture, corneocytes cannot have normal metabolism, and conditions of keratoderma and skin peeling and cell shedding are prone to occur, likely causing dermatitis and producing a sense of discomfort of itching, pain, and burning, even resulting in dry fine lines. On the other hand, melanin is the most relevant element in determining darkness or lightness of the skin color. Melanin exists in the normal skin and is a protein produced inside melanin cells. The produced melanin is transported and dispersed to the surrounding 36 corneocytes, and will gradually fall off as the corneocytes go through natural metabolism. Any change in the producing process of melanin, in the steps in which the melanin is packaged and assigned to each corneocyte, or in the degradation speed of melanin, will affect the darkness or lightness of the skin color.

Therefore, skin hydration and melanin elimination are two main points in skin care and skin detection. However, analysis methods to detect different skin areas are not exactly the same. If another skin area analysis method or a wrong analysis method is applied to a certain skin area, detection inaccuracy will occur.

SUMMARY OF THE INVENTION

The invention provides a skin condition detection method, an electronic apparatus, and a skin condition detection system, ensuring that a correct analysis method corresponding to the detected area is used while detecting the skin condition so that the skin condition may be accurately detected.

The skin condition detection method of the invention is adapted to detect a skin condition of each of a plurality of facial areas by a detection apparatus. The skin condition detection method includes the following steps: providing an action prompt, wherein the action prompt prompts to place the detection apparatus on one of the plurality of facial areas; detecting a user action corresponding to the detection apparatus; determining if the user action including the detection apparatus corresponds to the facial area prompted by the action prompt; and when the user action including the detection apparatus corresponds to the facial area prompted by the action prompt, analyzing the skin condition of the facial area by a skin analysis method corresponding to the facial area.

The electronic device of the invention is adapted to detect a skin condition of each of a plurality of facial areas. The electronic apparatus includes a storage device, an image capturing device, and a processor. The storage device is configured to store a plurality of modules. The image capturing device is configure to capture a plurality of images. The processor is coupled to the storage device and the image capturing device, and is configured to access and execute the plurality of modules stored by the storage device. The plurality of modules includes a prompt module, an action detection module, a determination module, and an analysis module. The prompt module provides an action prompt, wherein the action prompt prompts to place a detection apparatus on one of the plurality of facial areas. The action detection module detects a user action corresponding to the detection apparatus by the plurality of captured images. The determination module determines if the user action including the detection apparatus corresponds to the facial area prompted by the action prompt. The analysis module, when the user action including the detection apparatus corresponds to the facial area prompted by the action prompt, analyzes the skin condition of the facial area by a skin analysis method corresponding to the facial area.

The skin condition detection system of the invention includes a detection apparatus and an electronic apparatus. The detection apparatus is configured to detect a skin condition of each of a plurality of facial areas. The electronic apparatus includes a communication device, a storage device, an image capturing device, and a processor. The communication device is configured to communicate with the detection apparatus. The storage device is configured to store a plurality of modules. The image capturing device is configured to capture a plurality of images. The processor is coupled to the storage device, the image capturing device, and the communication device, and is configured to access and execute the plurality of modules stored by the storage device. The plurality of modules includes a prompt module, an action detection module, a determination module, and an analysis module. The prompt module provides an action prompt, wherein the action prompt prompts to place the detection apparatus on one of the plurality of facial areas. The action detection module detects a user action corresponding to the detection apparatus by the plurality of captured images. The determination module determines if the user action including the detection apparatus corresponds to the facial area prompted by the action prompt. The analysis module, when the user action including the detection apparatus corresponds to the facial area prompted by the action prompt, obtains a detection result of the detection apparatus by the communication device. And based on the detection result, the analysis module calculates the skin condition by using a skin analysis method corresponding to the facial area. The skin analysis method corresponding to each of the plurality of facial areas is different from each other.

Based on the above, in the embodiments of the invention, the skin condition detection method, the electronic apparatus, and the skin condition detection system use the image capturing device to capture the user's images, and analyze the images to identify the user action so as to further determine if the user correctly places the detection apparatus on the facial area to be detected. In this way, while calculating the skin condition, the correct skin analysis method corresponding to the facial area can be used in order to detect the skin condition of the user accurately.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
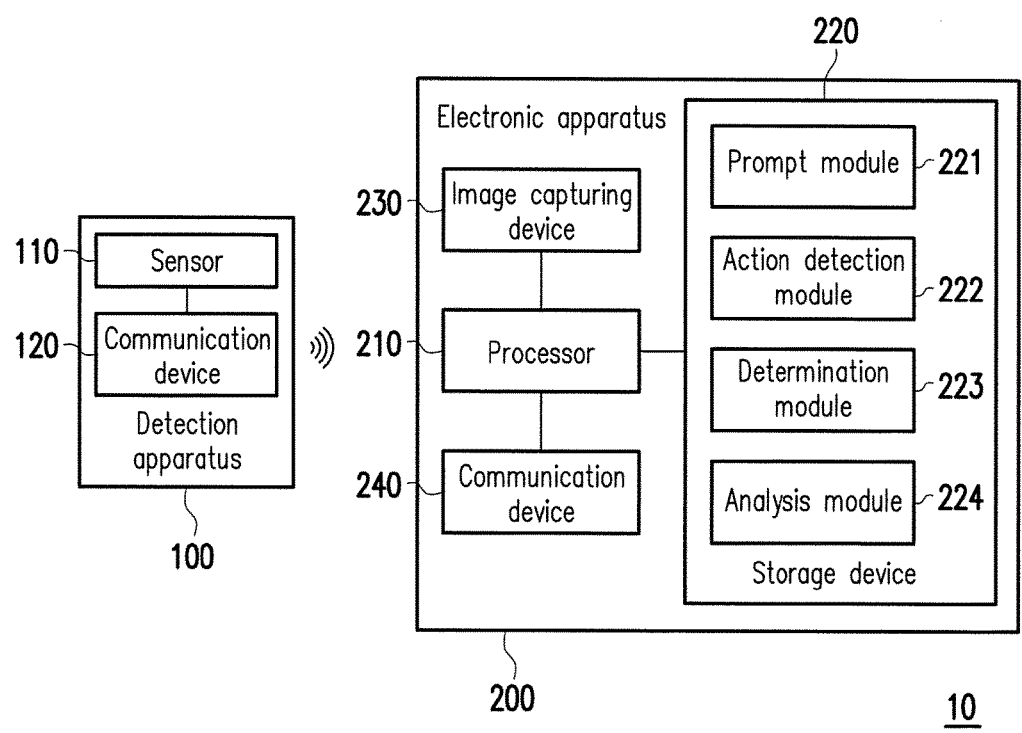
FIG. 1 illustrates a schematic block diagram of a skin condition detection system according to an embodiment of the invention.

FIG. 1 illustrates a schematic block diagram of a skin condition detection system according to an embodiment of the invention. With reference to FIG. 1, in this embodiment, a skin condition detection system 10 includes a detection apparatus 100 and an electronic apparatus 200. The electronic apparatus 200 in the embodiments of the invention may be provided on a mirror of a dressing table. Therefore, when a user looks in the mirror and uses the detection apparatus 100 to detect a skin condition of a facial area, the electronic apparatus 200 captures and analyzes an action image of the user performing detection so as to analyze the user's skin condition by using a skin analysis method corresponding to the facial area being detected. In this embodiment, the skin analysis method corresponding to each facial area is different from each other.

In this embodiment, the detection apparatus 100 includes at least one sensor 110 configured to detect a skin condition such as hydration or melanin of the skin. By placing the detection apparatus 100 on different facial areas, the user may detect the skin condition of the different facial areas. In this embodiment, the detection apparatus 100 further includes a communication device 120 coupled to the sensor 110 and configured to communicate with the electronic apparatus 200 of the skin condition detection system 10 so as to transmit a detection result to the electronic apparatus 200.

In this embodiment, the electronic apparatus 200 at least includes a processor 210, a storage device 220, an image capturing device 230, and a communication device 240. The processor 210 is coupled to the storage device 220, the image capturing device 230, and the communication device 240. It should be noted that in other embodiments, the electronic apparatus 200 may also be an electronic product such as a smartphone, a tablet computer or a desktop computer, or a portable mirror case in combination with a portable mirror.

The processor 210 may be a central processing unit (CPU), a microprocessor, a digital signal processor, a programmable logic controller, an application specific integrated circuit (ASIC), a programmable logic device (PLD), or other devices with a data computing function.

The storage device 220 may be any type of fixed or portable random access memory (RAM), read-only memory (ROM), flash memory, or similar components, or a combination of the above components. In this embodiment, the storage device 220 is configured to store a prompt module 221, an action detection module 222, a determination module 223, and an analysis module 224. The above modules are, for example, computer programs stored in the storage device 220 that may be loaded into the processor 210 so that the processor 210 may perform functions of a skin condition detection method as described in the embodiments of the application accordingly. It is worth noting that the storage device 200 in this embodiment is not limited to be a single memory component, and that each of the foregoing modules may be stored separately in two or more memory components of the same type or of different types. In other embodiments of the invention, the foregoing modules are also implemented, for example, by specific circuit configurations respectively.

The image capturing device 230 may be a camera equipped with a charge coupled device (CCD), a complementary metal-oxide semiconductor (CMOS) component, or other kinds of photosensitive component so as to be configured to capture a plurality of images of the user performing skin care, especially images of the facial and neck areas.

The communication device 240 may be a wireless communication module such as a Bluetooth module, and communicates wirelessly with the communication device 120 of the detection apparatus 100. In other embodiments, the communication device 240 may also communicate with the detection apparatus 100 in a wired manner.

The skin condition detection method provided by the embodiments of the invention is applicable to the skin condition detection system 10 as shown in FIG. 1. In the following, embodiments will be provided in combination with the skin condition detection system 10 as shown in FIG. 1 to illustrate the skin condition detection method. It should be noted that the skin condition detection method is not limited to be applied to the skin condition detection system 10, and other electronic apparatuses or systems and detection apparatuses with corresponding capabilities may likewise implement the foregoing skin condition detection method. In the following, embodiments are provided to illustrate detailed steps and procedures of this method.

Figure 2:
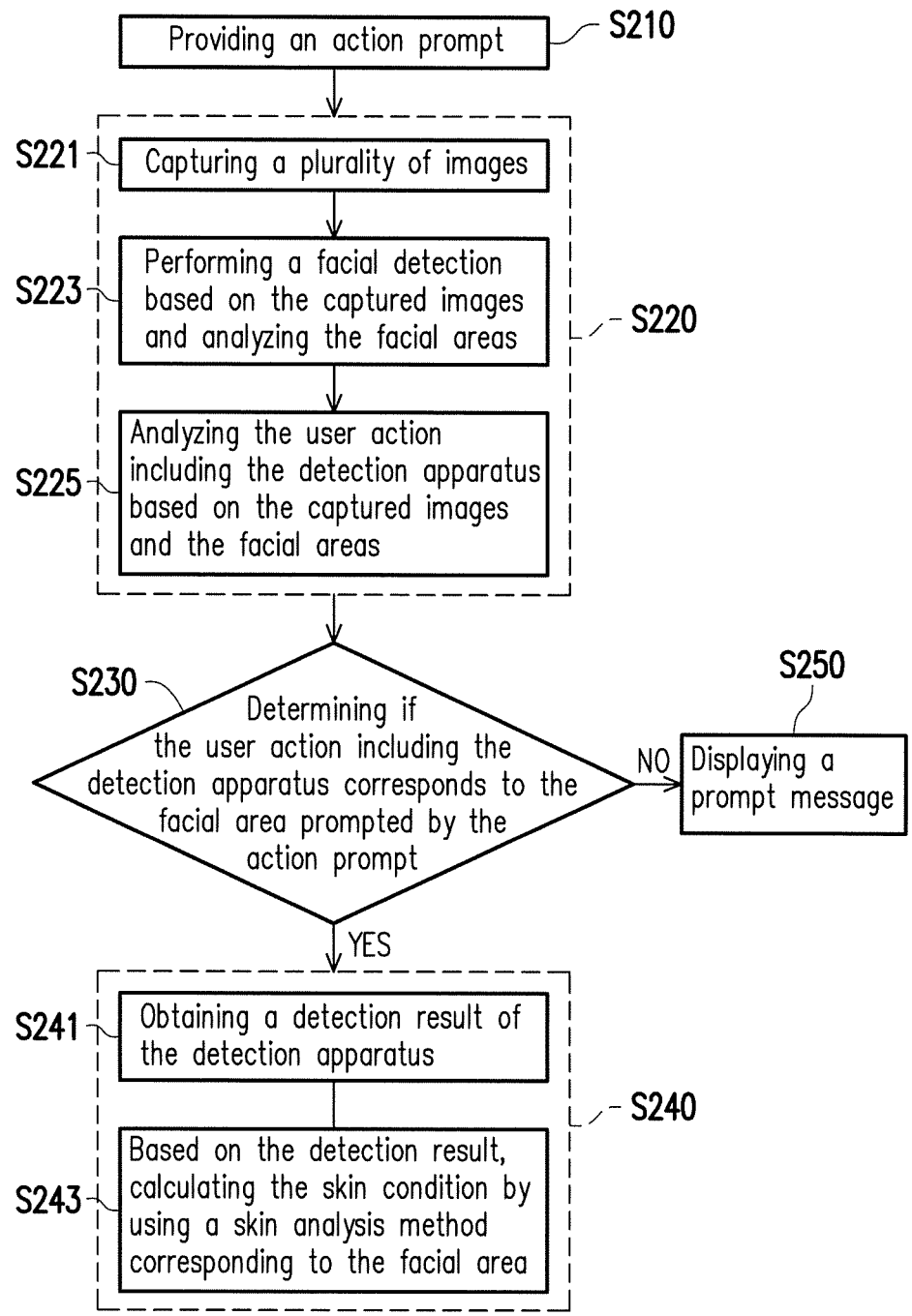
FIG. 2 illustrates a flowchart of a skin condition detection method according to an embodiment of the invention.
Figure 3:
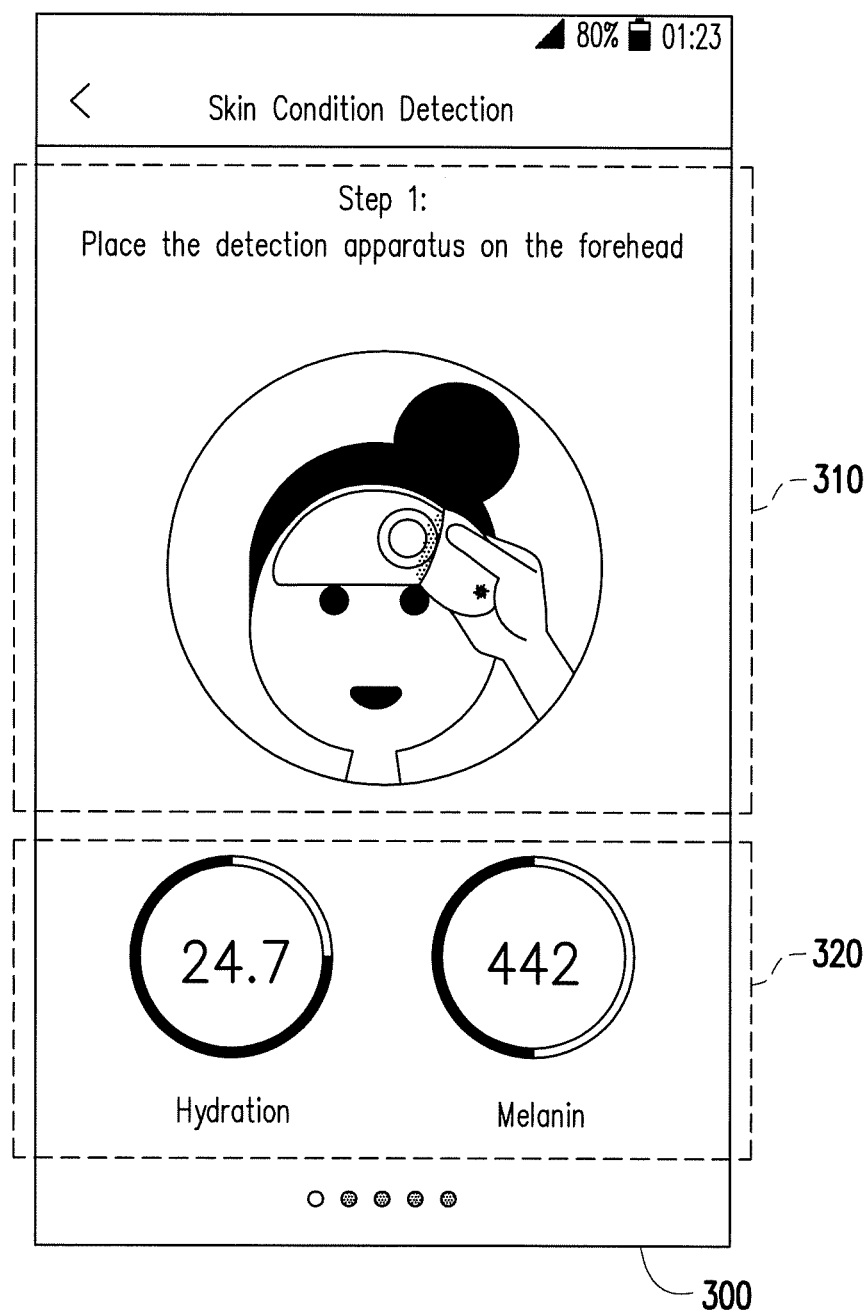
FIG. 3 illustrates a schematic view of a skin condition detection method according to an embodiment of the invention.

FIG. 2 illustrates a flowchart of a skin condition detection method according to an embodiment of the invention. FIG. 3 illustrates a schematic view of a skin condition detection method according to an embodiment of the invention. In this embodiment, the processor 210, for example, uses a display device (not shown) provided behind a mirror to display a detection screen 300 as shown in FIG. 3. The detection screen 300 further includes an action prompt area 310 and an analysis result area 320.

In step S210, the processor 210 executes the prompt module 221 to provide an action prompt. Herein the action prompt prompts to place the detection apparatus 100 on one of a plurality of facial areas. In this embodiment, the action prompt area 310 of the detection screen 300 provides a prompt that the portion currently to be detected is the forehead, therefore prompting the user to place the detection apparatus 100 on the forehead. In this embodiment, the plurality of facial areas may include, for example, the forehead, the left eye, the right eye, the left cheek, the right cheek, the chin, and the neck. During the detection process, the user is prompted to perform detection on the facial areas one by one using the detection apparatus 100, but the invention is not limited thereto.

In other embodiments, for performing detection on the plurality of facial areas, a facial image may also be displayed in the action prompt area 310 of the detection screen 300, and the prompted facial area is marked by a different color. For example, in the detection screen 300, the forehead area of the facial image may be marked with a yellow block, and the user is prompted to place the detection apparatus 100 on the area marked in yellow.

Then, in step S220, the processor 210 executes the action detection module 222 to detect a user action corresponding to the detection apparatus 100. Specifically, the detection apparatus 100 has a specific appearance or mark, and the image capturing device 230 of the electronic apparatus 200 captures a plurality of images consecutively. Based on the plurality of captured images, the action detection module 222 detects the user action corresponding to the detection apparatus 100 therefrom so as to determine if the user has placed the detection apparatus 100 on the facial area as prompted in step S210.

It is worth noting that a user action in this embodiment may include, for example, target object information, action information, and facial area information. For example, the user may wipe the right cheek with a cotton swab. In this example, the target object information is the "cotton swab," the action information is "wiping," and the facial area information is the "right cheek." For another example, the user may place the detection apparatus 100 on the forehead. In this example, since the detection apparatus 100 has a specific appearance or mark, the processor 210 is able to identify by analysis that the target object information is the "detection apparatus 100," the action information is "placing," and the facial area information is the "forehead." However, the invention is not limited thereto. In other embodiments, the user action may also include more information or less information (for example, besides the target object information, information of left and right hands is also included to indicate that the user is currently using the left hand or the right hand to operate the target object). A person skilled in the art may define the information contained in the user action in accordance with the requirement.

In this embodiment, step S220 further includes steps S221 to S225. In step S221, the action detection module 222 captures a plurality of images consecutively by the image capturing device 230. In this embodiment, it is after the processor 210 providing the action prompt in step S210 that the image capturing device 230 begins to capture the images and the processor 210 analyzes the images. However, in other embodiments, the image capturing device 230 may also be continuously capturing images with a specific frequency right after the electronic apparatus 200 is powered up. The embodiments of the invention are not limited thereto.

In step S223, based on the captured images, the action detection module 222 performs a facial detection to identify by analysis a plurality of facial areas. Specifically, the action detection module 222 performs the facial detection on the captured images so as to determine if there is at least one human face in the images and then goes on to select one human face therefrom as an analysis target. In this embodiment, the action detection module 222 uses a plurality of feature points of the human face (for example, 119 points, but not limited thereto) to identify by analysis the human face in the images, and then identifies by analysis the plurality of facial areas such as the forehead, left and right cheeks, left and right eyes, the nose or the chin according to such feature points. In this way, in step S223, the action detection module 222 may select the human face that serves as the analysis target and analyze the plurality of facial areas therefrom.

Then, in step S225, based on the respective images and the identified facial area, the action detection module 222 analyzes the user action including the detection apparatus 100. Specifically, the action detection module 222 performs an image analysis on the captured images to find out whether there is a target object functioning in the facial area identified by analysis in step S223. For example, when the user wipes the right cheek with a cotton swab, the action detection module 222 identifies by analysis that the target object is a cotton swab, and the cotton swab is acted on the right cheek. After information of the captured images is analyzed as described above, the action detection module 222, from the captured images, integrates the consecutive images including the same target object acted on the same facial area, so as to analyze the user action corresponding to each image. A user action may be identified by analysis based on information of the plurality of consecutive images.

To take "wiping the right cheek with a cotton swab" as an example, since the action of wiping is a continuous process, if a cotton swab acting on the right cheek, including the movement of wiping, is identified by analysis in each of the consecutive images, then the consecutive images correspond to the user action of "wiping the right cheek with a cotton swab."

To take "placing the detection apparatus 100 on the forehead" as an example, while it is impossible to observe consecutive different actions from the consecutive images as far as the action of placing is concerned, information of a plurality of images is still needed so that "placing" and "wiping" may be differentiated in order to further determine that the action information is "placing." Consequently, in this embodiment, if the detection apparatus 100 acting on the forehead is identified by analysis in each of the consecutive images, and if the position where the detection apparatus 100 acts on the forehead stays the same in each of the consecutive images, then the action detection module 222 determines that the consecutive images correspond to the user action of "placing the detection apparatus 100 on the forehead."

In one embodiment, the storage device 220 further includes a database (such as Table 1 below), in which a plurality of user actions and the action numerals thereof are recorded. In step S225, the processor 210 further compares if the identified user action matches the user actions recorded in the database. If the answer is yes, then the identified user action is viewed as a qualified user action that proceeds to be analyzed. If the answer is no, it is viewed as no action.

TABLE 1

| Action Numeral | User Action |
| --- | --- |
| NoAction | No Action |
| Action_1 | Wiping the right cheek with a cotton swab |
| Action_2 | Placing the detection apparatus on the forehead |

In this way, the action detection module 222 is able to identify by analysis the corresponding user actions in the images. As long as the user action that has the "detection apparatus 100" as the target object is further selected therefrom, the user action including the detection apparatus 100 may be identified by analysis.

Then, in step S230, the processor 210 executes the determination module 223 to determine if the user action including the detection apparatus 100 as described above corresponds to the facial area prompted by the action prompt. In this embodiment, the action prompt in step S210 prompts the user to place the detection apparatus 100 on the forehead. Consequently, in step S230, the determination module 223 may, for example, determine if there is any user action that has the action information of "placing" and the facial area information of the "forehead" among the user actions including the detection apparatus 100 that have been identified by analysis in step S220.

In this embodiment, after the action prompt is prompted in step S210, if, within a predetermined time, no user action corresponding to the detection apparatus is detected in step S220, or no user action including the detection apparatus 100 and corresponding to the facial area prompted by the action prompt is detected in step S230, the processor 210 then prompts the user by the prompt module 221. In this embodiment, the processor 210 then proceeds to step S250, displaying a prompt message of detection failure by the display device behind the mirror. But the embodiments of the invention are not limited thereto. In other embodiments, the processor 210 may also return to step S210, asking the user to place the detection apparatus 100 on the facial area prompted by the action prompt.

In this embodiment, if it is determined in step S230 that there is a user action including the detection apparatus 100 and corresponding to the facial area prompted by the action prompt, then the processor 210 proceeds to step S240 and executes the analysis module 224 to analyze the skin condition of the facial area by using the skin analysis method corresponding to the facial area. In this embodiment, step S240 further includes step S241 and step S243.

In step S241, the analysis module 224 obtains a detection result of the detection apparatus 100 by the communication device 240. In this embodiment, the detection apparatus 100 is configured to detect the skin condition including hydration and melanin. Consequently, after obtaining the detection result of the detection apparatus 100, the analysis module 224 then proceeds to step S243 and, based on the detection result, calculates numerical values associated with skin conditions such as hydration and melanin by using the skin analysis method corresponding to the "forehead." In this embodiment, as shown in FIG. 3, the processor 210 further displays the calculated analysis result in the analysis result area 320 of the detection screen 300 by the display device behind the mirror.

Finally, in this embodiment, the processor 210 further executes the prompt module 221 to prompt the unanalyzed facial areas among the plurality of facial areas. For example, the facial areas of this embodiment include the forehead, the left eye, the right eye, the left cheek, the right cheek, the chin, the neck and so on. Consequently, after the detection of the skin condition of the forehead is finished, the prompt module 221 further continues to provide action prompts to prompt the user to place the detection apparatus 100 sequentially on the unanalyzed facial areas of the left eye, the right eye, the left cheek, the right cheek, the chin, and the neck. In this way, the skin condition detection system 10 of this embodiment may accurately detect the skin condition of each facial area of the user.

In particular, after the skin condition of each facial area of the user is detected, the analysis result of the skin condition is further displayed in the display device by the prompt module 221.

Figure 4:
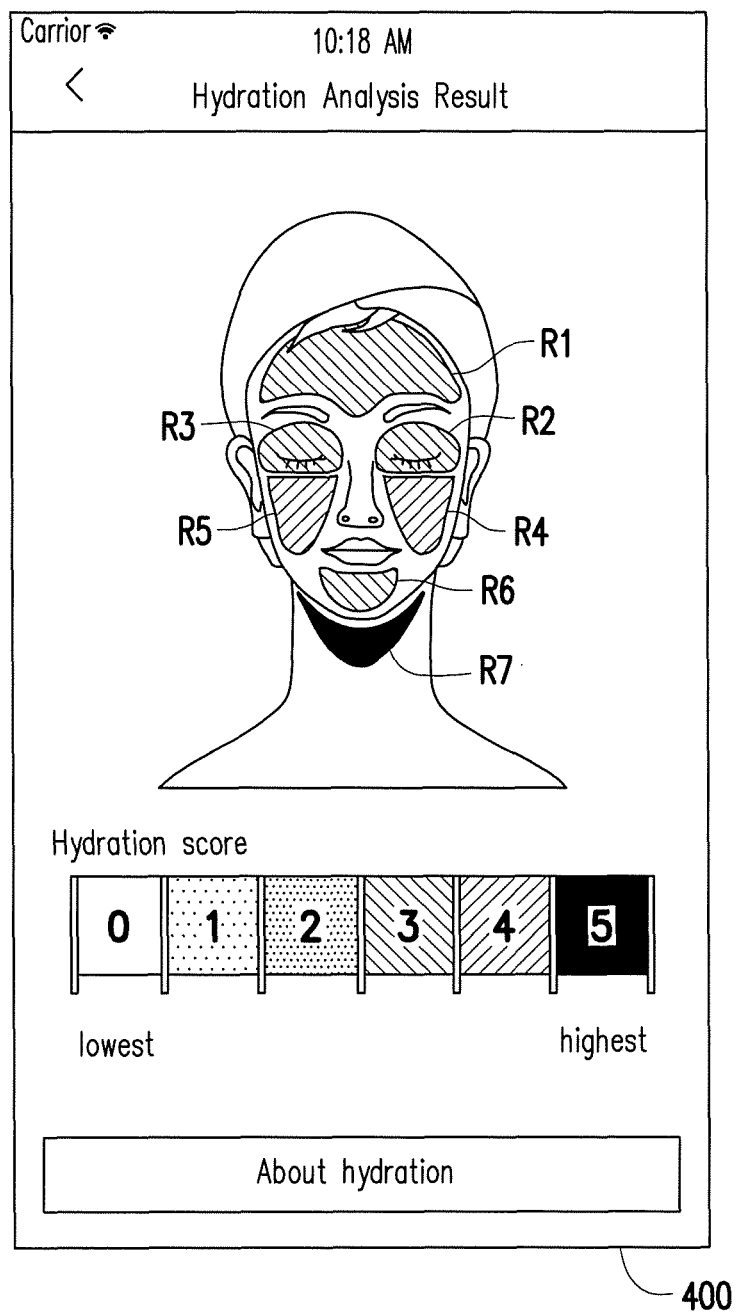
FIG. 4 illustrates a schematic view of a skin condition analysis result according to an embodiment of the invention.

FIG. 4 illustrates a schematic view of a skin condition analysis result according to an embodiment of the invention. With reference to FIG. 4, in this embodiment, after the skin condition detection system 10 finishes detecting the skin condition of each facial area, a skin condition analysis result 400 is generated.

To take hydration as an example, in this embodiment, based on detection results obtained from each of the facial areas of the forehead R1, the left eye R2, the right eye R3, the left cheek R4, the right cheek R5, the chin R6 and the neck R7, the processor 210 represents hydration using six hydration scores in a range of 0 to 5. Specifically, the hydration score is used to indicate the hydration level of the facial area. The higher the hydration score, the more moisturizing the facial area. Conversely, the lower the hydration score, the drier the facial area.

In this embodiment, the forehead R1, the left eye R2, and the right eye R3 each have a hydration score of 3 points, indicating that these facial areas have a moderate hydration level. The left cheek R4 and the right cheek R5 have a hydration score of 4 points, indicating that the facial areas of the left cheek R4 and the right cheek R5 have a good hydration level. The chin R6 has a hydration score of 3 points, indicating that the facial area of the chin R6 has a moderate hydration level. The neck R7 has a hydration score of 5 points, indicating that the facial area of the neck R7 has a terrific hydration level.

It is worth noting that the embodiment of FIG. 4 is exemplified by a hydration analysis result, but the invention is not limited thereto. In other words, each skin condition (such as melanin) detectable by the skin condition detection system 10 may generate a skin condition analysis result (such as a melanin analysis result).

In this way, by using the skin condition detection system 10 as described in the embodiments of the invention, the user may obtain the skin condition analysis result as shown in FIG. 4, and may clearly see the skin condition of each facial area therefrom to facilitate planning of future skin care procedures.

In summary, in the embodiments of the invention, the skin condition detection method, the electronic apparatus, and the skin condition detection system use the image capturing device to capture the user's images, and analyze the images to identify the user action so as to further determine if the user correctly places the detection apparatus on the facial area to be detected. In this way, while calculating the skin condition, the correct skin analysis method corresponding to the facial area can be used in order to detect the skin condition of the user accurately.

Although the embodiments are already disclosed as above, these embodiments should not be construed as limitations on the scope of the invention. It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A skin condition detection method adapted to detect a skin condition of each of a plurality of facial areas by an electronic apparatus, the skin condition detection method comprising:

providing an action prompt, wherein the action prompt prompts to place a detection apparatus on one of the plurality of facial areas;

capturing a plurality of images;

performing a facial detection based on the plurality of images to analyze the plurality of facial areas to detect a user action corresponding to the detection apparatus on the facial area;

determining if the user action corresponds to the facial area prompted by the action prompt; and when the user action corresponds to the facial area prompted by the action prompt, analyzing the skin condition of the facial area by a skin analysis method corresponding to the facial area, wherein the skin analysis method corresponding to each of the plurality of facial areas is different from each other.

2. The skin condition detection method as claimed in claim 1, wherein detecting the user action corresponding to the detection apparatus on the facial area comprises:

analyzing the user action comprising the detection apparatus based on the plurality of images and the plurality of facial areas.

3. The skin condition detection method as claimed in claim 1, wherein analyzing the skin condition of the facial area by the skin analysis method corresponding to the facial area comprises:

obtaining a detection result of the detection apparatus; and based on the detection result, calculating the skin condition by using the skin analysis method, wherein the skin condition comprises hydration and melanin.

4. The skin condition detection method as claimed in claim 1, further comprising:

prompting at least one unanalyzed facial area among the plurality of facial areas.

5. An electronic apparatus adapted to detect a skin condition of each of a plurality of facial areas, the electronic apparatus comprising:

a storage device configured to store a plurality of modules;

an image capturing device configured to capture a plurality of images; and a processor coupled to the storage device and the image capturing device, and configured to access and execute the plurality of modules stored by the storage device, the plurality of modules comprising:

a prompt module providing an action prompt, wherein the action prompt prompts to place a detection apparatus on one of the plurality of facial areas;

an action detection module detecting a user action corresponding to the detection apparatus on the facial area by the plurality of images, wherein the action detection module performs a facial detection based on the plurality of images captured by the image capturing device to analyze the plurality of facial areas;

a determination module determining if the user action corresponds to the facial area prompted by the action prompt; and an analysis module, when the user action corresponds to the facial area prompted by the action prompt, analyzing the skin condition of the facial area by a skin analysis method corresponding to the facial area, wherein the skin analysis method corresponding to each of the plurality of facial areas is different from each other.

6. The electronic apparatus as claimed in claim 5, wherein the action detection module, when detecting the user action corresponding to the detection apparatus on the facial area, analyzes the user action comprising the detection apparatus based on the plurality of images and the plurality of facial areas.

7. The electronic apparatus as claimed in claim 5, further comprising:

a communication device coupled to the processor and configured to communicate with the detection apparatus, wherein the analysis module, when analyzing the skin condition of the facial area by the skin analysis method corresponding to the facial area, obtains a detection result of the detection apparatus and, based on the detection result, calculates the skin condition by using the skin analysis method, wherein the skin condition comprises hydration and melanin.

8. The electronic apparatus as claimed in claim 5, wherein the prompt module further prompts at least one unanalyzed facial area among the plurality of facial areas.

9. A skin condition detection system, comprising:

a detection apparatus configured to detect a skin condition of each of a plurality of facial areas; and an electronic apparatus comprising:

a communication device configured to communicate with the detection apparatus;

a storage device configured to store a plurality of modules;

an image capturing device configured to capture a plurality of images; and a processor coupled to the storage device, the image capturing device, and the communication device, and configured to access and execute the plurality of modules stored by the storage device, the plurality of modules comprising:

a prompt module providing an action prompt, wherein the action prompt prompts to place the detection apparatus on one of the plurality of facial areas;

an action detection module detecting a user action corresponding to the detection apparatus on the facial area by the plurality of images, wherein the action detection module performs a facial detection based on the plurality of images captured by the image capturing device to analyze the plurality of facial areas;

a determination module determining if the user action corresponds to the facial area prompted by the action prompt; and an analysis module, when the user action corresponds to the facial area prompted by the action prompt, obtaining a detection result of the detection apparatus by the communication device; and based on the detection result, calculating the skin condition by using a skin analysis method corresponding to the facial area, wherein the skin analysis method corresponding to each of the plurality of facial areas is different from each other.

* * * * *